(12) United States Patent
Moser et al.

(10) Patent No.: US 9,327,145 B2
(45) Date of Patent: May 3, 2016

(54) COSMETIC COMPOSITIONS COMPRISING MANIKARA MULTINERVIS AND EXTRACTS THEREOF

(75) Inventors: Philippe Moser, Dommartemont (FR); Christine Jeanmaire, Nancy (FR); Vincent Bardey, Nancy (FR); Louis Danoux, Saulxures les Nancy (FR)

(73) Assignee: Cognis IP Management GmbH, Duesseldorf (DE)

( * ) Notice: Subject to any disclaimer, the term of this patent is extended or adjusted under 35 U.S.C. 154(b) by 442 days.

(21) Appl. No.: 13/392,981

(22) PCT Filed: Jan. 26, 2010

(86) PCT No.: PCT/EP2010/000435
§ 371 (c)(1),
(2), (4) Date: May 29, 2012

(87) PCT Pub. No.: WO2011/023248
PCT Pub. Date: Mar. 3, 2011

(65) Prior Publication Data
US 2012/0244092 A1  Sep. 27, 2012

(30) Foreign Application Priority Data
Aug. 31, 2009 (EP) .................................... 09011147

(51) Int. Cl.
*A61K 36/15* (2006.01)
*A61K 8/02* (2006.01)
*A61Q 19/08* (2006.01)
*A61K 8/97* (2006.01)
*A61Q 5/00* (2006.01)

(52) U.S. Cl.
CPC . *A61Q 19/08* (2013.01); *A61K 8/97* (2013.01); *A61Q 5/00* (2013.01)

(58) Field of Classification Search
CPC .................................. A61K 8/02; A61K 36/15
USPC ................................................. 424/770, 725
See application file for complete search history.

(56) References Cited

U.S. PATENT DOCUMENTS 4,146,615 A * 3/1979 Fauran et al. .................. 424/764
5,840,943 A   11/1998 Ansmann et al.

FOREIGN PATENT DOCUMENTS

| DE | 19712033 | 9/1998 |
|---|---|---|
| EP | 0766661 B1 | 8/1999 |
| JP | 2001-151634 | 6/2001 |
| JP | 2001-316221 | 11/2001 |
| JP | 2002-241300 | 8/2002 |
| JP | 2004-067551 | 3/2004 |
| JP | 2006-062989 | 3/2006 |
| JP | 2006-111541 | 4/2006 |
| JP | 2006-298812 | 11/2006 |
| JP | 2008-260761 | 10/2008 |

OTHER PUBLICATIONS

Burkhill, H.M., "Manikara multinervervis" vol. 5-XP-002568101 2000, 1 page.*
Diallo et al. "Wound healing Plants in Mali, the Bamako Region. An Ethanobotanical Survey and Complement Fixation of Water Extracts from Selected Plants", Pharmaceutical Biology, 2002, vol. 40, No. 2, pp. 117-128.*
"Commission Directive 2005/9/EC", *Official Journal of the European Union* 2005, 2 pgs.
PCT International Search Report in PCT/EP2010/000435, dated Apr. 27, 2010, 1 pgs.
Burkill, H. M., "Manilkara multinervis", vol. 5—XP-002568101 2000, 1 pg.
Fiedler, Herbert P., "Lexikon der Hilfsstoffe fur Pharmazie, Josmetik und angrenzende Gebiete", 4 Auflage 1996, 2 pgs.
Finkel, P., "Formulierung josmetischer Sonnenschutzmittel", *SOFW-Journal*, 122 1996, 543-548.
Finkel, P., "Formulierung kosmetischer", Parfumerie und Kosmetik, 80 1999.
Griffin, William C., "Calculation of HLB Values of Non-Ionic Surfactants", *Journal of the Society of Cosmetic Chemists* 1954, 249-256.
Griffin, William C., "Classification of Surface-Active Agents by "HLB"", *Journal of the Society of Cosmetic Chemists* 1949, 311-326.
Kirk-Othmer,, "Encyclopedia of Chemical Technology", 3rd Edition, vol. 8 1979, 5 pgs.
Nurnberg, E. et al., "Hagers Handuch der pharmazeutischen Praxis", *5th Edition*, vol. 2 1991, 1029-1030.

* cited by examiner

*Primary Examiner* — Susan Hoffman
*Assistant Examiner* — Deborah Davis
(74) *Attorney, Agent, or Firm* — Servilla Whitney LLC

(57) ABSTRACT

The present invention is directed to cosmetic compositions comprising *Manilkara multinervis*, or an extract of *Manilkara multinervis*, and methods of using such compositions for skin and/or hair care, including skin and/or hair protection, and/or skin and/or hair regeneration.

14 Claims, No Drawings

COSMETIC COMPOSITIONS COMPRISING MANIKARA MULTINERVIS AND EXTRACTS THEREOF

CROSS-REFERENCE TO RELATED APPLICATIONS

This application is the National Phase entry of International Application No. PCT/EP2010/000435, filed Jan. 26, 2010, which claims priority to European Patent Application No. EP 09011147.7, filed Aug. 31, 2009, each of which is incorporated by reference in its entirety.

FIELD OF THE INVENTION

The invention pertains to plants, plant extracts and their use in cosmetic compositions, particularly *Manilkara multinervis*, extracts of *Manilkara multinervis*, and their use in cosmetic compositions.

BACKGROUND OF THE INVENTION

There are a number of cosmetic compositions available to consumers to improve the aspect of the skin. In particular these cosmetics are used to prevent or to fight against skin ageing signs such as loss of firmness, decrease of skin thickness, fine lines, wrinkles, loss of elasticity, sagging, diminished rate of turnover, and abnormal desquamation. These effects are intensified by years of exposure to UV rays, irritants, allergens, and various environmental toxins. Such cosmetic compositions are generally designated as anti-ageing compositions.

The skin consists of three layers, the epidermis, the dermis and the subcutaneous tissue (hypodermis). The skin's extracellular matrix is a complex network of macromolecules, such as collagen or elastic fibers, glycoproteins, glycosaminoglycans and proteoglycans. It provides a physical framework to assume mechanical strength and participates in cell metabolism regulation.

SUMMARY OF THE INVENTION

Embodiments of the present invention provide a plant and/or cosmetic composition which can be used for the preparation of or in cosmetic compositions. The plant and/or a cosmetic composition can be used as an anti-ageing compound and/or composition. In particular embodiments the plant and/or cosmetic compositions can be used to improve skin firmness and/or to improve skin smoothness and/or to ameliorate or prevent signs of skin ageing and/or to ameliorate or prevent stretch marks and/or to ameliorate the quality of scalp dermis and/or to fight against scalp ageing.

DETAILED DESCRIPTION OF THE INVENTION

The invention pertains to the use of *Manilkara multinervis*, preferably extracts thereof and cosmetic compositions comprising *Manilkara multinervis* and extracts thereof. It has surprisingly been found that *Manilkara multinervis*, preferably *Manilkara multinervis* extracts, can be used for the preparation of or in cosmetic compositions.

Thus one embodiment of the invention is directed to the use of *Manilkara multinervis* for the preparation of or in a cosmetic composition.

A preferred cosmetic use is for skin and/or hair care, skin and/or hair protection, and/or skin and/or hair regeneration. The effects, especially the anti-ageing effects, of *Manilkara multinervis*, preferably *Manilkara multinervis* extract, on skin and skin cells encompass the improvement of skin appearance, the improvement of the skin firmness, the prevention and/or the reduction of skin ageing signs. Such skin ageing signs are selected, e.g., from the group consisting of decrease of skin thickness, fine lines, wrinkles, loss of elasticity, sagging, diminished rate of turnover, and abnormal desquamation. UV protection and/or the prevention and/or reduction of photoageing signs is also encompassed. The skin anti-ageing effect of *Manilkara multinervis* encompasses to increase the skin's regenerative and renewal process, to rejuvenate the aged or stressed human skin, to improve age-related loss of turn-over, and/or to strengthen the skin extracellular matrix network. More generally, it encompasses to improve the skin firmness, to prevent and/or to diminish intrinsic and/or extrinsic skin ageing, to delay the outcome of wrinkles, to reduce the depth of installed wrinkles, to diminish the appearance of fine lines and/or to improve the skin aspect and/or tone. Advantageously, the skin anti-ageing effect is combined of more than one or even all of these effects.

*Manilkara multinervis*, its extracts and cosmetic compositions comprising them are especially suitable as anti-ageing compounds or compositions. Thus one embodiment of the invention is directed to the use of *Manilkara multinervis*, its extracts and cosmetic compositions as anti-ageing compounds or compositions In the complex process of skin-ageing, many metabolic pathways are involved. It was one aim of the present invention to provide a plant, preferably an extract thereof and/or a cosmetic composition comprising them which effectively acts on at least one of the pathways involved in skin ageing, preferably in two or more pathways. One embodiment of the invention is directed to the cosmetic use of *Manilkara multinervis*, preferably extracts of *Manilkara multinervis* and compositions comprising them as elastase inhibitors and/or as stimulators of collagen production and/or for the deceleration or prevention of non-enzymatic glycation. One embodiment of the invention is directed to the cosmetic use of *Manilkara multinervis*, preferably extracts of *Manilkara multinervis* and compositions as anti-ageing compounds and/or composition, comprising them as elastase inhibitors and/or as stimulators of collagen production and/or for the deceleration or prevention of non-enzymatic glycation.

*Manilkara multinervis*, its extracts and cosmetic compositions comprising them are especially suitable for improving skin firmness and/or improving skin smoothness and/or ameliorating or preventing signs of skin ageing and/or ameliorating or preventing stretch marks and/or ameliorating the quality of scalp dermis and/or fighting against scalp ageing.

Thus one embodiment of the invention is directed to the use of *Manilkara multinervis*, preferably extracts of *Manilkara multinervis* and compositions comprising them, to improve skin firmness and/or to improve skin smoothness and/or to ameliorate or prevent signs of skin ageing and/or to ameliorate or prevent stretch marks and/or to ameliorate the quality of scalp dermis and/or to fight against scalp ageing.

TERMS AND DEFINITIONS

As used in the context of present invention, the singular forms of "a" and "an" also include the respective plurals unless the context clearly dictates otherwise. Thus, the term "a" or "an" is intended to mean "one or more" or "at least one", unless indicated otherwise.

"Comprising" in the context of present invention means that the components listed after the word "comprising" are either the sole components forming the composition (i.e. the composition consist of said components), or that in addition to said components at least one further component is present. In a preferred meaning, it means "consisting essentially of", and in its narrowest meaning, it is synonymous to "consisting of"

The term "anti-ageing" is widely used in the cosmetic industry and typically means delaying or lessening the effects of ageing (e.g. of chronological ageing, photoageing or ageing due to other adverse environmental factors besides UV radiation) on the skin. With age and exposure to adverse environmental factors, the visual appearance, physical properties, and physiological functions of skin change in ways that are considered cosmetically undesirable. The most notable and obvious changes include the development of fine lines and wrinkles, loss of elasticity, increased sagging, loss of firmness, loss of color evenness (tone), coarse surface texture, and mottled pigmentation. Less obvious, but measurable changes which occur as skin ages or endures chronic environmental insult include a general reduction in cellular and tissue vitality, reduction in cell replication rates, and a reduction in the skin's ability to remodel and repair itself. Anti-ageing compounds and compositions are designed to prevent, delay, revert (at least partially), lessen or decrease these changes. The anti-ageing effect of compounds and compositions may be evaluated by conventional panel tests which are standard practice in the cosmetic industry.

The term "skin" refers to the skin of an animal or human, preferably a mammalian skin or—even more preferred—human skin. "Skin" encompasses the epidermis, the dermis and the hypodermis. The term "skin cells" pertains to any cell typically present in the skin, e.g. a cell of the group consisting of keratinocytes, fibroblasts, endothelial cells, basal cells, granular cells, Merkel cells, melanocytes, Langerhans cells, leukocytes, mastocytes, nerve cells, adipose cells and macrophages. In the context of present invention, fibroblasts and/or keratinocytes are preferred, and fibroblasts are particularly preferred. Furthermore, human skin cells, particularly human fibroblasts and/or keratinocytes are preferred.

The term "ameliorate" or "amelioration" includes the arrest, prevention, decrease, or improvement in one or more of the signs, features or symptoms of the indicated condition, may it be temporary or long-term.

*Manilkara multinervis*

*Manilkara multinervis* (Bak.) Dubard (family Sapotaceae) is an African shrub or medium-sized tree, 4 to 10-15 m high with a trunk more or less expanded at the base. The bark is deeply fissured and scaly, grey to dark brown and exudes a white latex. The leaves are alternate and collected at the ends of branches. They are elliptical to obovate, 7-14 cm long and 4-7 cm wide with a pointed or rounded top. Distribution areas of *Manilkara multinervis* are African forests and savannas from Senegal to Cameroon.

In one embodiment of the invention, *Manilkara multinervis* can be used directly, e.g. plant parts such as bark or leaves. In a preferred embodiment of the invention an extract of *Manilkara multinervis* is used.

The term "extract" is intended to pertain both to the liquid resulting from the extraction step according to present invention and to the intermediate and final product (which typically is a dry product) of the process for preparation of the extract according to present invention. The appropriate meaning is generally clear from the context. Each of the liquid extract, the intermediate and the final product may be used in the context of present invention, e.g. in a composition or use according to present invention. But the final product, especially the dried final product or a composition comprising said final product is preferred.

The term "plant part" refers to any part or parts of a plant taken either individually or in a group. Examples include leaves, flowers, roots, seeds, pods, stems, fruits, seed coats, buds and other parts of a plant. In the context of present invention, leaves and leaves containing plant parts are preferred.

Preparation of the Extract

The *Manilkara multinervis* extract according to the invention may be prepared by known methods of extracting plants or parts thereof. Suitable extraction processes, such as maceration, re-maceration, agitation maceration, digestion, vortex extraction, ultrasonic extraction, countercurrent extraction, percolation, re-percolation, evacolation (extraction under reduced pressure), diacolation, continuous solid/liquid extraction, can be found for example in Hagers Handbuch der pharmazeutischen Praxis (5$^{th}$ Edition, Vol. 2, pp 1029-1030, Springer-Verlag, Berlin-Heidelberg-New York, 1991). Extraction can also be conducted under subcritical or supercritical conditions, using as solvents e.g. carbon dioxide, water with or without alcohol or glycols.

In general, the extraction process entails an extraction step, i.e. contacting solid plant material with a solvent with adequate mixing and for a period of time sufficient to ensure adequate exposure of the solid plant material to the solvent. Preferably, said period of time is sufficient to ensure that compounds conferring the desired properties in the plant material can be taken up by the solvent.

The solvent for the extraction of the *Manilkara multinervis* plant or plant parts may be any solvent suitable for extraction of plants or plant parts and is preferably selected from the group consisting of aqueous solvents (such as water or an aqueous buffer) and organic apolar or polar solvents such as low molecular weight alcohols, e.g. from the group consisting of methanol, ethanol, propylene glycol, butylene glycol, pentylene glycol, pentane, hexane, heptane, acetone, ethyl methyl ketone, ethyl acetate, mixtures thereof and water-containing mixtures thereof, more preferably from the group consisting of water and organic polar solvents such as methanol, ethanol, butylene glycol, mixtures thereof and water-containing mixtures thereof. Even more preferably, the solvent is selected from the group consisting of mixtures of an aqueous solvent, especially water, with one or more polar organic solvent, preferably with a water-miscible organic solvent, more preferably with a low molecular weight alcohol. A mixture of water with an organic solvent selected from the group consisting of 1,3-butyleneglycol, methanol, ethanol, and mixtures thereof is especially preferred.

In a preferred aspect, the extract is obtained by alcoholic or hydroalcoholic extraction, particularly by extraction with a solvent selected from the group consisting of water, methanol, ethanol and water-containing mixtures thereof, specifically water/ethanol and water/methanol mixtures, more specifically water/ethanol mixtures.

When the extraction process is carried out using a water-containing mixture, i.e. a mixture of an aqueous solvent with an organic solvent, the content of the organic solvent in the mixture ranges from 5% to 95% by volume, preferably from 40 to 90% (v/v). A content of organic solvent from 60 to 80% (v/v), especially of 70% (v/v) is particularly preferred.

For uses wherein the extract will be formulated for application to the skin, a solvent that is compatible with said skin may be selected. Examples of such solvents include water, aqueous buffers, a low molecular weight alcohol, and a mixture of an aqueous solvent with a low molecular weight alcohol.

A "low molecular weight alcohol" is an alcohol having 1 to 5 carbon atoms and may be a primary, secondary or tertiary alcohol. It may be a mono- or polyalcohol, with mono-, di- and trialcohols being preferred, monoalcohols, glycols and glycerine being especially preferred. Accordingly, the low molecular weight alcohol may preferably be selected from the group consisting of methanol, ethanol, 1-propanol, 1-butanol, 2-propanol, 2-butanol, 2-methyl-1-propanol, 2-methyl-2-propanol, pentanol, glycerine, ethylene glycol, diethylene glycol, dipropylene glycol, propylene glycol, 1,3-butylene glycol, pentylene glycol, and mixtures thereof. In the context of present invention methanol, ethanol, propylene glycol, butylene glycol, and pentylene glycol are especially preferred.

The extraction process is generally carried out at a temperature from 4 to 180° C., preferably from 20 to 150° C., more preferably from 20 to 100° C., most preferably 60 to 100° C. Extraction at room temperature or under reflux—i.e. at the boiling temperature of the solvent—is particularly preferred.

The extraction process may be carried out in an inert gas atmosphere to avoid oxidation of the active principles of the extract.

The extraction process is generally performed at a pH from 2.5 to 11, preferably from 4 to 9, more preferably at light acidic or neutral pH. In a specific preferred aspect, when the solvent is water, the pH is preferably adjusted to an acidic or neutral pH, more preferably a pH from 4 to 8, even more preferably from 4.5 to 7.5. The adjustment may be achieved by addition of any acid or base which is suitable to achieve the required pH, but addition of pH adjusting agents which are cosmetically acceptable ingredients is preferred. In one aspect, the pH is lowered by addition of sulfuric acid.

The plant material may be pretreated prior to the extraction process in order to facilitate the extraction process. Typically, these pretreatment results in plant material being fragmented, such that a greater surface area is presented to the solvent. For example, the plant material can be crushed or sliced mechanically, using a grinder or other fragmenting device.

The particle size of the raw material and the extraction times are routinely selected by the expert in dependence upon the extraction process, the solvent, the temperature and pH conditions, and the ratio of solvent to raw material, etc. Generally, an extraction time of from 40 min to 20 h, preferably of about 1 to 2 h is sufficient. The extraction process may be carried out to any degree, but is usually continued to exhaustion.

During or after the extraction process, the crude extracts may be subjected to other typical purification and workup steps, such as for example purification, clarification, concentration, decoloration, and/or enzymatic hydrolysis. Preferably, such steps take place after the extraction step.

In one preferred aspect, an enzymatic hydrolysis is performed during or after the extraction process. In said aspect, a hydrolytic enzyme is added to the extraction mixture. Said enzyme is preferably a protease, more preferably a protease used in food or feed industry, most preferably Alcalase® or a protease with similar enzymatic properties. When an enzyme is added, the preferred solvent is water or an aqueous mixture. Preferably, the pH is at or about the pH optimum of the protease. Generally, the pH is a pH from 4 to 9, preferably from 6 to 8.5, most preferably a pH at about 7.5.

If desired, the extract thus prepared may be subjected to further purification steps, using membrane separation techniques such as nanofiltration, ultrafiltration, precipitation techniques, adsorption/desorption techniques on resins, and/or chromatography techniques.

If desired, the extract may be subjected, for example, to the selective removal of individual unwanted ingredients. Alternatively, an extraction method is selected whereby unwanted ingredients are extracted from the plant material only in a reduced amount or not at all, e.g. by using a hydroalcoholic or alcoholic extraction solvent.

If desired, the extract may be subjected to drying processes, for example to spray drying or freeze drying. In the context of present invention, the *Manilkara multinervis* extract is preferably dried before its use in skin treatment.

In a preferred embodiment of the invention the *Manilkara multinervis* extract
(i) an extract of a leaf or a leaf containing plant part, and/or
(ii) is an aqueous or hydroalcoholic extract The term "hydroalcoholic" is synonymous to "aqueousalcoholic". Typical yields of dry matter extracted from the raw plant material based on the quantity of raw material used are in the range from 0.5 to 40% by weight (w/w) and more particularly in the range from 2 to 20% (w/w). The extraction conditions and the yields of the final extracts may be selected by the expert according to the desired application.

The extract may be mixed with one or more auxiliaries, such as e.g. mannitol, sorbitol, maltodextrine, cyclodextrine, glycerine, sugars as saccharose, fructose, glucose and trehalose.

A further embodiment of the invention is directed to a method for preparing a *Manilkara multinervis* extract, comprising a step wherein a *Manilkara multinervis* whole plant or plant part is extracted, preferably by aqueous or hydroalcoholic extraction.

Cosmetic Composition

One embodiment of the invention is directed to a cosmetic composition comprising
a) *Manilkara multinervis*, preferably an extract of *Manilkara multinervis*
b) at least one cosmetically acceptable carrier The cosmetic composition comprises *Manilkara multinervis*, preferably an extract of *Manilkara multinervis* in an effective amount, i.e. in such an amount that the desired effect is achieved. The cosmetic composition can comprise *Manilkara multinervis*, preferably an extract of *Manilkara multinervis*, in a concentration of 0.0001 to 90%, more preferably in a concentration of 0.001 to 70%, especially in a concentration of 0.001 to 50%—based on the total weight of the composition. In a preferred embodiment of the invention, the cosmetic composition comprises *Manilkara multinervis* or an extract thereof in a concentration from 0.0001 to 10% and more preferentially from 0.001 to 5%, even more preferentially from about 0.01 to about 2% by weight based on the total weight of the composition.

The composition according to the invention is a cosmetic composition. For the distinction between cosmetic and pharmaceutical compositions and their corresponding use, reference is made to the legal provisions of the German Federal Republic of Germany (e.g. Kosmetikverordnung, Lebensmittel- and Arzneimittelgesetz).

"Cosmetic composition" shall mean any preparation intended to be placed in contact with the various external parts of the human body (e.g. skin particularly epidermis), hair, nails, lips) or with the teeth and the mucous membranes of the oral cavity with a preferred view exclusively or mainly to cleaning them, perfuming them, changing their appearance and/or correcting body odours and/or protecting them or keeping them in good condition.

The cosmetic composition according to the invention can be in a wide variety of types, e.g. in form of a solution (e.g. aqueous solution, water free system such as e.g. oil), dispersion, emulsion and combinations thereof. Emulsions generally contain an aqueous phase and an oil phase. Typical emulsion types are oil-in-water emulsions, water-in-oil emulsions, silicone-in-water emulsions, and/or a water-in-silicone emulsion.

Examples of cosmetic compositions are body care and cleansing composition, such as body oil, baby oil, body milk, creams, lotions, sprayable emulsions, sunscreens, antiperspirants, liquid and bar soaps, as well as surfactant-containing compositions, such as, for example, foam and shower baths, hair shampoos and hair care rinses. They may be applied as a care component to tissues, papers, wipes, nonwovens, sponges, puffs, plasters and bandages which are used in the field of hygiene and care (wet wipes for baby hygiene and baby care, cleaning wipes, facial wipes, skin care wipes, care wipes containing active ingredients against ageing of the skin, wipes containing sun protection formulations and insect repellents and wipes for decorative cosmetics or for after-sun treatment, toilet wipes, antiperspirant wipes, diapers, handkerchiefs, wet wipes, hygiene products, self-tanning wipes). They may also be used inter alia in hair-care, hair-cleaning or hair-coloring compositions. They may furthermore also be used in decorative cosmetics, such as lipsticks, lipglosses, foundations, make-up, pressed and loose powders, eyeshadow, mascaras and the like.

The term "cosmetically acceptable carrier" as used herein, means that the carrier is suitable for use in contact with human keratinous tissue without undue toxicity, incompatibility, instability, allergic response, and the like. In a further embodiment of the invention the cosmetically acceptable carrier is selected from the group consisting of at least one solvent (b-1), at least one surface-active substance (b-2) and/or at least one wax component (b-3) and/or at least one polymer (b-4) and/or at least one oil component (b-5).

Thus one embodiment of the invention is directed to a cosmetic composition comprising
a) *Manilkara multinervis*, preferably an extract of *Manilkara multinervis* and
b) at least one cosmetically acceptable carrier, wherein the cosmetically acceptable carrier is selected from the group consisting of at least one solvent (b-1), at least one surface-active substance (b-2) and/or at least one wax component (b-3) and/or at least one polymer (b-4) and/or at least one oil component (b-5).

Solvent (b-1)

In one embodiment of the invention the cosmetically acceptable carrier is at least one solvent (b-1). A suitable solvent is such a solvent that was used for the preparation of the extract. Thus in one embodiment of the invention the cosmetically acceptable carrier is selected from the group consisting of water, a low molecular weight alcohol and mixtures thereof. In a preferred embodiment of the invention the solvent is selected from the group consisting of water, methanol, ethanol, 1-propanol, 1-butanol, 2-propanol, 2-butanol, 2-methyl-1-propanol, 2-methyl-2-propanol, pentanol, glycerine, ethylene glycol, diethylene glycol, dipropylene glycol, propylene glycol, 1,3-butylene glycol, pentylene glycol, and mixtures thereof.

Surface-Active Substances (b-2)

In one embodiment of the invention, the compositions according to the invention comprise at least one surface-active substance. Surface-active substances are all substances which lower the interfacial tension between the aqueous and the non-aqueous phase. Surface-active substances include emulsifiers and surfactants.

In one embodiment of the invention, the composition according to the invention comprise more than one surface-active substance. Depending on the other components, the expert uses typical systems (such as, for example, emulsifier and co-emulsifier).

The compositions according to the invention can contain the surface-active substance(s) in a quantity of 0 to 80 weight-%, preferably 0.1 0 to 40 weight-%, preferably 0.1 to 20 weight-%, preferably 0.1 to 15 weight-% and more particularly 0.1 to 10 weight-%, based on the total weight of the composition.

A suitable emulsifier is in principle any surface-active substance, but in particular substances with an HLB value of from 1 to 20 according to the Griffin scale. Each emulsifier is assigned a so-called HLB value (a dimensionless number between 1 and 20 Griffin scale) which indicates whether a preferred solubility in water or oil is present. Numbers below 9 indicate preferably oil-soluble, hydrophobic emulsifiers; numbers above 11 water-soluble, hydrophilic emulsifiers. The HLB value says something about the equilibrium of the size and strength of the hydrophilic and of the lipophilic groups in an emulsifier. The Griffin scale is described in W C Griffin, J. Soc. Cosmet. Chem. 1 (1949) 311; W C Griffin, J. Soc. Cosmet. Chem. 5 (1954) 249. The HLB value of an emulsifier can also be calculated from increments, where the HLB increments for the various hydrophilic and hydrophobic groups from which a molecule is composed. As a rule, it can be found in tables (e.g. H. P. Fiedler, Lexikon der Hilfsstoffe für Pharmazie, Kosmetik and angrenzende Gebiete [Lexion of Auxiliaries for Pharmacy, Cosmetics and Related Fields], Editio Cantor Verlag, Aulendorf, $4^{th}$ edition, 1996) or the manufacturers' information. The solubility of the emulsifier in the two phases practically determines the type of emulsion. If the emulsifier is more soluble in water, then an O/W emulsion is obtained. By contrast, if the emulsifier has better solubility in the oil phase, then under otherwise identical preparation conditions, a W/O emulsion is formed.

Nonionic Emulsifiers:

The group of nonionic emulsifiers includes, for example,
(1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;
(2) $C_{12-18}$ fatty acid monoesters and diesters of products of the addition of 1 to 50 mol ethylene oxide onto glycerol;
(3) sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) products of the addition of 7 to 60 mol ethylene oxide onto castor oil and/or hydrogenated castor oil;
(6) polyol esters and, in particular, polyglycerol esters such as, for example, polyolpoly-12-hydroxystearate, polyglycerol polyricinoleate, polyglyceryl-4-laurate, polyglycerol diisostearate or polyglycerol dimerate. Mixtures of compounds from several of these classes are also suitable;
(7) products of the addition of 2 to 15 mol ethylene oxide onto castor oil and/or hydrogenated castor oil;
(8) partial esters based on linear, branched, unsaturated or saturated $C_{6-22}$ fatty acids, ricinoleic acid and 12-hydroxystearic acid and polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) or mixed esters, as well as sucrose polystearate (commercially available as Emulgade® SUCRO from Cognis).

(9) polysiloxane/polyalkyl polyether copolymer or corresponding derivatives;

(10) mixed esters of pentaerythritol, fatty acids, citric acid and fatty alcohol and/or mixed esters of fatty acids containing 6 to 22 carbon atoms, methyl glucose and polyols, preferably glycerol or polyglycerol.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. These emulsifiers are w/o or o/w emulsifiers, depending on the degree of ethoxylation. $C_{12/18}$ fatty acid monoesters and diesters of addition products of ethylene oxide onto glycerol are known as lipid layer enhancers for cosmetic compositions.

According to the invention, particularly suitable and mild emulsifiers are the polyol poly-12-hydroxystearates and mixtures thereof marketed by Cognis Deutschland GmbH under the name of "Dehymuls® PGPH" (w/o emulsifier) or "Eumulgin® VL 75" (mixture with Coco Glucosides in a ratio by weight of 1:1, o/w emulsifier) or "Dehymuls® SBL" (w/o emulsifier). Particular reference is made in this connection to EP 0 766 661 B1. The polyol component of these emulsifiers may be derived from substances which contain at least two, preferably 3 to 12 and more particularly 3 to 8 hydroxyl groups and 2 to 12 carbon atoms.

In principle, suitable lipophilic w/o emulsifiers are emulsifiers with an HLB value of 1 to 8 which are listed in numerous tables and are well-known to the expert. Some of these emulsifiers are listed, for example, in Kirk-Othmer, "Encyclopedia of Chemical Technology", 3rd Edition, 1979, Vol. 8, page 913. The HLB value for ethoxylated products may also be calculated to the following formula: HLB=(100−L):5, where L is the percentage by weight of lipophilic groups, i.e. fatty alkyl or fatty acyl groups, in percent by weight in the ethylene oxide adducts.

Of particular advantage from the group of w/o emulsifiers are partial esters of polyols, more particularly $C_{4-6}$ polyols, such as for example partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

Depending on the formulation, it can also be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example 10-20 ethylene oxide units for o/w emulsifiers and 20-40 ethylene oxide units for so-called solubilizers. Particularly advantageous o/w emulsifiers for the purposes of the invention are Ceteareth-12, Cetheareth-20 and PEG-20 Stearate. Particularly suitable solubilizers are Eumulgin® HRE 40 (INCI name: PEG-40 Hydrogenated Castor oil), Eumulgin® HRE 60 (INCI name: PEG-60 Hydrogenated Castor Oil), Eumulgin® L (INCI name: PPG-1-PEG-9 Laurylglycolether) and Eumulgin® SML 20 (INCI name: Polysorbat-20).

Nonionic emulsifiers from the group of alkyl oligoglycosides are particularly compatible with the skin. $C_{8-22}$ alkyl mono- and oligoglycosides, their production and their use are known from the prior art. They are produced in particular by reacting glucose or oligosaccharides with primary alcohols containing 6 to 24, preferably 8 to 22 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based. Products available under the name of Plantacare® or Plantaren® contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the name of Emulgade® PL 68/50 by Cognis Deutschland GmbH, which is a 1:1 mixture of alkyl polyglucosides and fatty alcohols, is preferred for the purposes of the invention. According to the invention, the mixture of Lauryl Glucoside, Polyglyceryl-2-Dipolyhydroxystearate, glycerol and water which is marketed as Eumulgin® VL 75 may also be used with advantage in accordance with the invention.

Other suitable emulsifiers are such substances as lecithins and phospholipids. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are generally classed as fats. Sphingosines and sphingolipids are also suitable as fat-like substances.

Silicone emulsifiers, for example, may be present as emulsifiers. These can be selected, for example, from the group of alkylmethicone copolyols and/or alkyldimethicone copolyols, in particular from the group of compounds which are characterized by the following chemical structure:

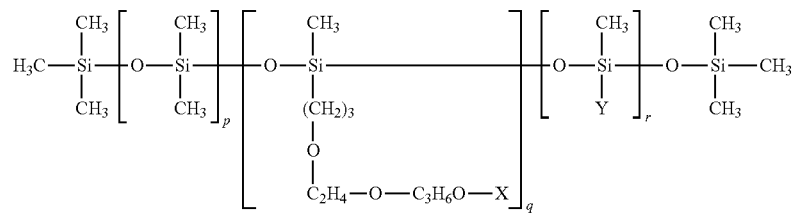

in which X and Y, independently of one another, are selected from the group H (hydrogen) and the branched and unbranched alkyl groups, acyl groups and alkoxy groups having 1-24 carbon atoms, p is a number from 0-200, q is a number from 1-40, and r is a number from 1-100. One example of silicone emulsifiers to be used particularly advantageously within the context of the present invention are dimethicone copolyols, which are sold by Evonik Goldschmidt under the trade names ABIL® B 8842, ABIL® B 8843, ABIL® B 8847, ABIL® B 8851, ABIL® B 8852, ABIL® B 8863, ABIL® B 8873 and ABIL® B 88183. A further example of interface-active substances to be used particularly advantageously within the context of the present invention is cetyl PEG/PPG-10/1 dimethicone (Cetyl Dimethiconecopolyol), which is sold by Evonik Goldschmidt under the trade name ABIL® EM 90. A further example of interface-active substances to be used particularly advantageously within the context of the present invention is the cyclomethicone dimethiconecopolyol, which is sold by Evonik Goldschmidt under the trade name ABIL® EM 97 and ABIL® WE 09. Furthermore, the emulsifier Lauryl PEG/PPG-18/18 Methicone (laurylmethicone copolyol) has proven to be very particularly advantageous and is available under the trade name Dow Corning® 5200 Formulation Aid from Dow Corning Ltd. Furthermore a silicone emulsifier with the INCI name "Cyclopentasiloxane and PEG/PG-18-18 Dimethicone" has proven to be advantageous, it is available for example under the tradename Dow Corning® 5225 C Formulation Aid.

A further advantageous silicone emulsifier is Octyl Dimethicone Ethoxy Glucoside from Wacker. For a water-in-silicone oil emulsion according to the invention, all known emulsifiers used for this type of emulsion can be used. According to the invention, particularly preferred water-in-silicone emulsifiers here are cetyl PEG/PPG-10/1 dimethicones and lauryl PEG/PPG-18/18 methicones [e.g. ABIL® EM 90 (Evonik Goldschmidt), DC5200 Formulation Aid (Dow Corning)] and any desired mixtures of the two emulsifiers.

A suitable anionic O/W emulsifier is for example Disodium Cetearyl Sulfosuccinate (commercially available under the tradename Eumulgin® Prisma).

Surfactant(s):

In one embodiment of the invention, the compositions according to the invention comprise as surface-active substance at least one surfactant. The surfactant(s) may be selected from anionic, nonionic, cationic and/or amphoteric or zwitterionic surfactants. Surfactant-containing cosmetic compositions, such as for example shower gels, foam baths, shampoos etc., preferably contain at least one anionic surfactant.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable, particularly as co-surfactants. Ampholytic surfactants are surface-active compounds which, in addition to a C$_{8-18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids (commercially available under the tradename Dehyton®DC), N-hydroxyethyl-N-alkyl-amidopropyl glycines, N-alkyl taurines, N-alkyl sarcosines, 2-alkylaminopropionic acids and alkylamino acetic acids containing around 8 to 18 carbon atoms in the alkyl group. Particularly preferred ampholytic surfactants are N-cocoalkylaminopropionate, cocoacylaminoethyl aminopropionate and C$_{12/18}$ acyl sarcosine. Suitable are furthermore N-alkyliminodipropionic acid derivatives such as Sodium N-Lauryl-beta-Iminodipropionate, commercially available under the tradename Deriphat® 160 C. Suitable are furthermore Amphoacetates such as e.g. Cocoamphoacetates (e.g. Dehyton® MC) or Cocoamphodiacetates (e.g. Dehyton® DC). Anionic surfactants are characterized by a water-solubilizing anionic group such as, for example, a carboxylate, sulfate, sulfonate or phosphate group and a lipophilic group. Dermatologically safe anionic surfactants are known to the expert in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear C$_{12-18}$ alkyl or acyl groups and sulfosuccinates and acyl glutamates in the form of their alkali metal or ammonium salts. Particularly suitable anionic surfactants are Glyceryl stearate citrate (commercially available as Imwitor®370, Imwitor® 372P, Axol®C,62 or Dracorin®CE 614035) and/or glyceryl stearate lactate. Examples of suitable alkyl sulfates are for example Sodium Cetearyl Sulfate (commercially available as Lanette® E), examples of suitable phosphates are Potassium Cetyl Phosphate (commercially available as Amphisol® K). Examples of suitable acyl glutamates are Sodium Stearoyl Glutamate (commercially available as Eumulgin® SG). A further example of a suitable anionic surfactant is Sodium Lauryl Glucose Carboxylate (commercially available as Plantapon® LGC). Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Suitable are furthermore pseudo cationic surfactants such as stearylaminopropyl ditmethylamine (commercially available under the tradename Dehyquart®S18 or Incromine®SB or TegoAmideeS18). In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates. Suitable cationic surfactants are for example Dipalmitoylethyl Hydroxyethylmonium Methosulfate (tradename Dehyquart®C4046), Distearoylethyl Hydroxyethylmonium Methosulfate (tradename Dehyquart®F75), Dicocoylethyl Hydroxyethylmonium Methosulfate (tradename Dehyquart® L80), Behentrimonium Chloride (tradename Varisoft® BT), Distearyldimonium Chloride (tradename Varisoft® TA 100), Palmitamidopropyltrimonuim Chloride (tradename Varisoft® PATC).

Wax Component b-3

In one embodiment of the invention, the preparations according to the invention comprise at least one wax component. The compositions according to the invention can comprise the wax component(s) in a quantity of 0 to 40 weight-%, more particularly 0 to 20 weight-%, preferably 0.1 to 15 weight-% and more particularly 0.1 to 10 weight-%, based on the total weight of the composition. Waxes are normally understood to be natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. A single wax component or a mixture of wax components melting at or above 30° C. may be used in accordance with the invention.

According to the invention, fats and fat-like substances with a wax-like consistency may also be used as waxes providing they have the required melting point. These include inter alia fats (triglycerides), mono- and diglycerides, natural and synthetic waxes, fat and wax alcohols, fatty acids, esters of fatty alcohols and fatty acids and fatty acid amides or mixtures of these substances. Fats in the context of the invention are understood to be triacylglycerols, i.e. the triple esters of fatty acids with glycerol. The triacylglycerols preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, shea butter are preferred. Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina®HR. Glycerol tristearate, glycerol tribehenate (for example Syncrowax®HRC), glycerol tripalmitate or the triglyceride mixtures known under the name of Syncrowax®HGLC are also suitable providing the melting point of the wax component or the mixture is 30° C. or higher.

According to the invention, suitable wax components are, in particular, mono- and diglycerides and mixtures of these partial glycerides. Glyceride mixtures suitable for use in accordance with the invention include the products Novata® AB and Novata® B (mixture of $C_{12-18}$ mono-, di- and triglycerides) and Cutina® HVG (Hydrogenated Vegetable Glycerides) or Cutina® GMS (glyceryl stearate) marketed by Cognis GmbH. The fatty alcohols suitable for use as a wax component in accordance with the invention include $C_{12-50}$ fatty alcohols. The fatty alcohols may be obtained from natural fats, oils and waxes such as, for example, myristyl alcohol, 1-pentadecanol, cetyl alcohol, 1-heptadecanol, stearyl alcohol, 1-nona-decanol, arachidyl alcohol, 1-heneicosanol, behenyl alcohol, brassidyl alcohol, lignoceryl alcohol, ceryl alcohol or myricyl alcohol. According to the invention, saturated unbranched fatty alcohols are preferred. However, unsaturated, branched or unbranched fatty alcohols may also be used as the wax component in accordance with the invention providing they have the required melting point. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols) or the partly branched alcohols from the oxosynthesis (Dobanols) may also be used. $C_{14-22}$ fatty alcohols marketed for example by Cognis Deutschland GmbH under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are particularly suitable for the purposes of the invention. Fatty alcohols give the compositions a dryer feeling on the skin than triglycerides. $C_{14-40}$ fatty acids or mixtures thereof may also be used as wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character. Waxes suitable for use in accordance with the invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids.

Examples of esters such as these include, for example, $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. Other suitable wax components which may be used are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

Polymers b-4

In one embodiment of the invention, the compositions according to the invention comprise at least one polymer. The compositions according to the invention can comprise the polymer(s) in a quantity of 0 to 20 weight-%, preferably 0.05 to 18 weight-%, preferably 0.05 to 15 weight-%, and, more particularly, 0.05 to 10 weight-%, more preferably 0.1 to 1 weight-%, based on the total weight of the composition. In a preferred embodiment of the invention, the polymers can be present in an amount of 0.1 to 5 weight-%, preferably 0.1 to 3 weight-% especially 0.1 to 2 weight-% based on the total weight of the composition. Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16, Jaguar®C 162 of Celanese, quaternary ammonium salt polymers such as, for example, Mirapol® A-15, Mirapol® AD-1, Mirapol® AZ-1 of Miranol. Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Especially suitable are anionic polymers with the INCI name Carbomer, like for example Carbopol of types 980, 980, 981, 1382, 2984, 5984 as well as Rheocare®C plus and Rheocare®400). Further suitable anionic polymers are those with the INCI name Acrylates/C10-30 Alkyl Acrylate Crosspolymer (e.g. Pemulen®TR, Pemulen® TR 2, Carbopol®Ultrez), Acrylates Copolymer (e.g. Rheocare TTA, TTN, TTN-2), Acrylamide/Sodium Acrylate Copolymer (e.g. Cosmedia®ATC), Sodium Polyacrylate (e.g. Cosmedia® ATH, Cosmedia®SP), Polyacrylamides (e.g. Sepigel® 305 or Sepigel® 501). Prefererred anionic polymers are Polyacrylic acid homo and co-polymers. Further suitable polymers are silicione elastomer gums, like for example silicone elastomer blends, such as blends with the INCI name Cyclolpentasiloxane (and) Dimethiconol (and) Dimethicone Crosspolymer, commercially available as Dow Corning®DC 9027, blends with the INCI name Isodecyl neopentanoate (and) Dimethicone/bis-isobutyl PPG-20 Crosspolymer, commercially available as Dow Corning®DC EL 8051 IN, blends with the INCI name Dimethicone/Vinyl Dimethicone Crosspolymer (and) C12-14 Pareth-12), commercially available as Dow Corning®DC 9509, and blends with the INCI name Dimethicone/Vinyl Dimethicone Crosspolymer (and) Silica, commercially available as Dow Corning®DC 9701 Cosmetic Powder. Other suitable polymers are polysaccharides, more particularly xanthan gum, guar gum, agar agar, alginates and tyloses as well as tara gum, carraghenane, sclerotium gum and natural cellulose.

Oil Components b-5

The cosmetic compositions according to the invention can comprise at least one oil component. The oil components are typically present in a total quantity of 0.1 to 95, preferably of 0.1 to 80, more particularly 0.5 to 70, preferably 1 to 60, more particularly 1 to 50 weight-%, more particularly 1 to 40 weight-%, preferably 5 to 25 weight-% and more particularly 5 to 15 weight-%. The oil components are typically present in a quantity of 0.1 to 40 weight-%. The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol), triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with polyols containing 2 to 10 carbon atoms and 2 to 6 hydroxyl groups, vegetable oils, branched primary alcohols, substituted cyclohexanes, linear and branches $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols and hydrocarbons or mixtures thereof.

Also suitable are esters of 2-propylheptanol with n-octanoate, a product which is commercially available under the tradename Cetiol®Sensoft (Cognis GmbH). Also suitable are hydrocarbons, such as for example undecan and tridecan. Also suitable are alkanes, such as for example INCI Coconut/Palm/Palm Kernel Oil Alkanes, commercially available as Vegelight 1214 from Biosynthesis).

At Least One Skin and/or Hair Care Active Ingredient (c)

In one embodiment of the invention the composition of the present invention comprise at least one additional skin and/or hair care active. A skin and/or hair care active is a substance that is useful for regulating and/or improving the condition of mammalian skin and/or hair.

Thus one embodiment of the invention is directed to a cosmetic composition comprising
 a) *Manilkara multinervis*, preferably an extract of *Manilkara multinervis*
 b) optionally at least one cosmetically acceptable carrier
 c) at least one skin and/or hair care active ingredient Classes of suitable skin care actives include, but are not limited to vitamins, peptides and peptide derivatives, sugar amines, UV-protective factors, flavonoid compounds, hair growth regulators, antioxidants and/or anti-oxidant precursors, preservatives, phytosterols, protease inhibitors, tyrosinase inhibitors, anti-inflammatory agents, and mixtures thereof. It should be noted, however, that many skin care actives may provide more than one benefit, or operate via more than one mode of action. Therefore, classifications herein are made for the sake of convenience and are not intended to limit the active to that particular application or applications listed.

Thus one embodiment of the invention is directed to a cosmetic composition comprising
 a) *Manilkara multinervis*, preferably an extract of *Manilkara multinervis*
 c) at least one at least one skin and/or hair care active ingredient, selected from the group consisting of vitamins (c-1), peptides and peptide derivatives (c-2), sugar amines (c-3), UV-protective factors (c-4) and/or flavonoid compounds (c-5).

Vitamins (c-1)

In one embodiment of the invention, the cosmetic composition comprises at least one vitamin. They may comprise 0001% to 50%, preferably 0.001% to 10%, more preferably 0.01% to 5%, and more preferably 0.1% to 1%, of one or more vitamins. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoid compounds such as retinol, retinyl acetate, retinyl palmitate, retinoic acid, retinaldehyde, retinyl propionate; carotenoids (pro-vitamin A); vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition comprises a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

Peptides and Peptide Derivatives (c-2)

In one embodiment of the invention, the cosmetic composition comprises at least one peptide and/or peptide derivative. Herein, "peptide" refers to peptides containing ten nr fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof.

Sugar Amine (c-3)

In one embodiment of the invention, the cosmetic composition comprises at least sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Sugar amine compounds useful in the present invention include, for example, N-acetyl-glucosamine. In one embodiment, the composition can comprise 0.01% to 15%, preferably 0.1% to 10%, and more preferably 0.5% to 5% of the sugar amine.

UV-Protective Factor (c-4)

In one embodiment of the invention, the cosmetic composition comprises at least one UV-protective factor. UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:
3-benzylidenecamphor (Mexoryl®SD) or 3-benzylidenenorcamphor (Mexoryl®SDS 20) and derivatives thereof, e.g. 3-(4-methylbenzylidene)camphor
3-(4'-Trimethylammonium)benzyliden-bornan-2-on-methylsulfat (Mexoryl® SO)
3,3'-(1,4-Phenylendimethin)-bis(7,7-dimethyl-2-oxobicyclo-[2.2.1]heptan-1-methansulfonsäure) and salts (Mexoryl®SX)
3-(4'-Sulfo)-benzyliden-bornan-2-on and salts (Mexoryl®SL)

Polymer of N-{(2und 4)-[2-oxoborn-3-yliden) methyl}benzyl]acrylamid (Mexoryl® SW)

2-(2H-Benzotriazol-2-yl)-4-methyl-6-(2-methyl-3-(1,3,3,3-tetramethyl-1-(trimethylsilyloxy)disiloxanyl)propyl)phenol (Mexoryl®XL)

4-aminobenzoic acid derivatives, preferably 2-ethylhexyl 4-(dimethylamino)benzoate, 2-octyl 4-(dimethylamino) benzoate and amyl 4-(dimethylamino)berizoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzalmalonate;

triazine derivatives, such as, for example, 2,4,6-trianilino(p-carbo-2'-ethyl-1'-hexyloxy)-1,3,5-triazine, or 2,4,6-Tris [p-(2-ethylhexyl-oxycar-bonyl) anilino]-1,3,5-triazin (Uvinul®T 150) or octyltriazone or (Uvasorb® HEB); or diethylhexyl butamido triazone (Uvasorb® HEB; =4,4'-[(6-[4-((1,1-Dimethylethyl)amino-carbonyl)phenyl-amino]-1,3,5-triazin-2,4-diyl)diimino]bis(benzoesaure-2-ethylhexylester)

2,2(-Methylen-bis(6-(2H-benzotriazol-2-yl)-4-(1,1,3,3-tetramethyl-butyl)phenol) (Tinosorb®M);

2,4-Bis[4-(2-ethylhexyloxy)-2-hydroxyphenyl]-6-(4-methoxyphenyl)-1,3,5-triazin (Tinosorb® S);

propane-1,3-diones, such as, for example, 1-(4-tert-butylphenyl)-3-(4'-methoxyphenyl)propane-1,3-dione;

ketotricyclo(5.2.1.0)decane derivatives, as disclosed in EP 0694521 B1.

Suitable water-soluble substances are:

2-phenylbenzimidazole-5-sulphonic acid and the alkali metal, alkaline earth metal, ammonium, alkylammonium, alkanolammonium and glucammonium salts thereof;

2,2(-(1,4-Phenylen)bis(1H-benzimidazol-4,6-disulfonic acid, monosodiumsalt) (Neo Heliopan®AP) (INCI: Disodium Phenyl Dibenzimidazole Tetrasulfonate)

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid and 2-methyl-5-(2-oxo-3-bornyl-idene)sulphonic acid and salts thereof.

In a preferred embodiment of the invention the compositions comprise at least one oil-soluble UV protective factor and at least one water-soluble UV protective factor.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoyl-methane (Parsol® 1789), 1-phenyl-3-(4'-isopropylphenyl)propane-1,3-dione, and enamine compounds, as disclosed in DE 19712033 A1 (BASF) as well as Benzoic Acid, 2-[4-(Diethylamino)-2-Hydroxybenzoyl]-, Hexyl Ester (Uvinul® A plus, INCI: Diethylamino hydroxybenzoyl hexyl benzoate. The UV-A and UV-B filters can of course also be used in mixtures. Particularly favourable combinations consist of the derivatives of benzoylmethane, e.g. 4-tert-butyl-4'-methoxydi-benzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts. Suitable UV-photoprotective factors are especially the ones listed in Annex VII of the Commissions Directive (in the Version Commission Directive 2005/9/EC of 28 Jan. 2005 amending Council Directive 76/768/EEC, concerning cosmetic products, for the purposes of adapting Annexes VII thereof to technical progress), which are hereby explicitly referred to. As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 Eusolex® T-Aqua, Eusolex® AVO, Eusolex® T-ECO, Eusolex® T-OLEO and Eusolex® T-S (Merck). Typical examples of zinc oxides are for example Zinc Oxide neutral, Zinc Oxide NDM (Symrise) or Z-Cote® (BASF) or SUNZnO-AS as well as SUNZnO-NAS (Sunjun Chemical Co. Ltd.). Suitable mixture comprising Titanium Dioxide are for example Cetiol® SUN (Cognis GmbH). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide. Further suitable UV protective factors listed in the review of P. Finkel in SÖFW-Journal 122, August/1996, p. 543 to 548 as well as in Parf. Kosm. 80. Jahrgang, Nr. March/1999, p. 10 to 16 are hereby included by reference. Besides the two groups of primary UV protection factors mentioned above, secondary UV protection factors of the antioxidant type may also be used. Secondary UV protection factors of the antioxidant type interrupt the photochemical reaction chain which is initiated when UV rays penetrate into the skin.

The compositions according to the invention can comprise the UV photoprotective factors in an amount of 0.1 to 30 weight-%, preferably 2.5 to 20 weight-%, more preferably 5-15 weight-%, based on the cosmetic composition Flavonoids (c-5)

In one embodiment of the invention, the cosmetic composition comprises at least one flavonoid. The compositions of the present invention may comprise a flavonoid. The flavonoid can be synthetic materials or obtained as extracts from natural sources, which also further may be derivatized. Examples of classes of suitable flavonoids include, but are not limited to, unsubstituted flavanones, methoxy flavanones, unsubstituted chalcones, and mixtures thereof. In one embodiment, the flavonoids are unsubstituted flavanones, unsubstituted chalcone (especially the trans-isomer), their glucosyl derivatives, and mixtures thereof. Other examples of suitable flavonoids include flavanones such as hesperidin compounds (e.g., glucosyl hesperidin), isoflavones such as soy isoflavones, including but not limited to genistein, daidzein, quercetin, and equol, their glucosyl derivatives, 2',4-dihydroxy chalcone, and mixtures thereof. The compositions of the present invention may comprise 0.01% to 20%, preferably 0.1% to 10%, and more preferably 0.5% to 5% of flavonoids.

Further Skin and/or Hair Care Actives

The compositions of the present invention further may comprise non-vitamin antioxidants and radical scavengers, minerals, preservatives, phytosterols and/or plant hormones, protease inhibitors, tyrosinase inhibitors, anti-inflammatory agents and N-acyl amino acid compounds. Suitable non-vitamin antioxidants and radical scavengers include, but are not limited to, BHT (butylated hydroxy toluene), L-ergothioneine (available as THIOTANE™); tetrahydrocurcumin, cetyl pyridinium chloride, carnosine, diethylhexyl syrinylidene malonate (available as OXYNEX™), hexadec-8-ene-1,16-dicarboxylic acid (octadecene dioic acid; ARLATONE™ Dioic DCA from Uniqema), ubiquinone (co-enzyme Q10), tea extracts including green tea extract, yeast extracts (e.g., Pitera®), yeast culture fluid, and combinations thereof. Suitable minerals include zinc, manganese, magnesium, copper, iron, selenium and other mineral supplements. "Mineral" is understood to include minerals in various oxidation states, mineral complexes, salts, derivatives, and combinations thereof. Suitable examples of plant sterols (phytosterols) and/or plant hormones include, but are not limited to, sitosterol, stigmasterol, campesterol, brassicasterol, kinetin, zeatin, and mixtures thereof. Suitable protease inhibitors include, but are not limited to, hexamidine, vanillin acetate, menthyl anthranilate, soybean trypsin inhibitor, Bowman-Birk inhibitor, and mixtures thereof. Suitable tyrosinase inhibitors include, but are not limited to, sinablanca (mustard seed extract), tetrahydrocurcumin, cetyl pyridinium chloride, and mixtures thereof. Suitable anti-inflammatory agents include, but are not limited to, glycyrrhizic acid (also known as glycyrrhizin, glycyrrhixinic acid, and glycyrrhetinic acid glycoside), glycyrrhetenic acid, other licorice extracts, and combinations thereof. Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE® from Seppic (France). Other useful skin care actives include moisturizing and/or conditioning agents, such as glycerol, petrolatum, caffeine, and urea; yeast extracts (for example, Pitera™); dehydroepiandrosterone (DHEA), its analogs and derivatives; exfoliating agents, including alpha- and beta-hydroxyacids, alpha-keto acids, glycolic acid and octanoyl salicylate; antimicrobial agents; antidandruff agents such as piroctone olamine, 3,4,4'-trichlorocarbanilide (trichlosan), triclocarban and zinc pyrithione; dimethyl aminoethanol (DMAE); creatine; skin lightening agents such as kojic acid, mulberry extract, hydroquinone, arbutin, and deoxy-arbutin; (sunless) tanning agents, such as dihydroxy acetone (DHA); plant-derived materials such as resveratol; isomers, salts, and derivatives of any of the foregoing; and mixtures thereof.

EXAMPLES

Examples 1 to 3

Preparation of an Extract of *Manilkara multinervis*

Example 1

3 Kg of crushed dry leaves of *Manilkara multinervis* were introduced in a steel reactor containing 30 liters of hot water. The suspension was extracted under shaking for one hour at 60° C. Then the mixture was cooled to room temperature. The liquid extract was separated from the insoluble fraction by centrifugation and subsequently clarified by filtration up to 0.45 μm. 17.6 liters of filtrate containing 16 g/l of extract were obtained and then concentrated under vacuum to 50-60 g/l of extract. Maltodextrine (100% by weight referring to the dry matter) was added to the solution.

The solution was then spray-dried to give 455 g of powder.

Example 2

200 g of crushed dry leaves of *Manilkara multinervis* were introduced in a glass reactor containing 2 liters of ethanol-water (70V-30V). The suspension was extracted under reflux for one hour. Then the mixture was cooled to room temperature. The liquid extract was separated from the insoluble fraction by filtration. Thereafter the alcohol was removed under reduced pressure at 35° C. and the residue was then freeze-dried. The yield of dry product was 18 to 20%, based on the dry weight of plants used.

Example 3

Example 2 was repeated except that extraction was carried out with 2 liters of ethanol 96%. After evaporation of ethanol the final product was dried in an oven under vacuum. The yield of dry product was 12.8 to 15.3%, based on the dry weight of plants used.

Examples 4 to 9

Efficacy of *Manilkara multinervis* Extracts

Example 4

Anti-Glycation Effect of *Manilkara multinervis* Extract

In order to evaluate the potential of *Manilkara multinervis* extract to reduce the rate of "non enzymatic" glycation of proteins such as skin collagen, the extract was tested in comparison to aminoguanidine as a positive reference. The "non-enzymatic" glycation results from the reaction of proteins with reducing sugars such as glucose and saccharose. These sugars react with the free amino groups present in the proteins to form the so called "Schiff's bases", ultimately resulting in so-called "advanced glycosylation endproducts". In human skin, the process of "non enzymatic" glycation causes in time a decrease of strength and an atrophy of dermis which are characteristic of skin aging.

The extracts were tested in vitro by incubating collagen type I in solution with glucose during 3 weeks at 45° C. Then the level of "non enzymatic" glycation was determined by measuring the rate of "Schiff's bases" through the record of fluorescence at 430 nm (excitation at 350 nm) of the supernatant solution recovered after centrifugation of the solutions during 15 minutes at 3500 rpm (revolution per minute). The rates of "non enzymatic" glycation were calculated as % referring to the control with glucose. The assays were repeated up to 6 times and the results were expressed in percentage referring to the control with glucose then presented as a mean+/− the SEM (standard error of mean) and statistically evaluated by the student t test. All % values given are weight-%.

Table 1 shows the results of the positive control, the results are expressed as rate of "Schiff's bases" in %/control with glucose:

|  | Rate of Schiff's bases in %/control with glucose |
|---|---|
| Control without glucose | 12 +/− 2 |
| Control with glucose | 100 +/− 0 |
| Glucose + Aminoguanidine at 0.02% | 47 +/− 1** (n = 6) |
| Glucose + Aminoguanidine at 0.05% | 34 +/− 1** (n = 6) |
| Glucose + Aminoguanidine at 0.1% | 27 +/− 1** (n = 6) |

Statistics:
(n = number of assays), student t test:
* = significant effect (p < 0.05);
** = very significant effect (p < 0.01).

The incubation of collagen with glucose has markedly increased the rate of "Schiff's bases". The "non enzymatic" glycation of collagen is distinctly reduced by aminoguanidine at 0.02%, 0.05% and 0.1%, this effect is significant and dose dependent.

Table 2 shows the results of the *Manilkara multinervis* extract according to example 1, the results are expressed as rate of "Schiff's bases" in %/control with glucose:

|  | Rate of Schiff's bases in %/control with glucose |
|---|---|
| Control without glucose | 12 +/− 2 (n = 6) |
| Control with glucose | 100 +/− 0 (n = 6) |
| Glucose + 0.01% extract | 58 (n = 1) |
| Glucose + 0.03% extract | 50 +/− 4** (n = 2) |
| Glucose + 0.1% extract | 43 +/− 3** (n = 6) |
| Glucose + 0.3% extract | 37 +/− 5** (n = 6) |

Statistics:
(n = number of assays), student t test:
* = significant effect (p < 0.05);
** = very significant effect (p < 0.01).

The incubation of collagen with glucose has markedly increased the rate of "Schiff's bases". *Manilkara multinervis* extract according to example 1 at 0.01-0.3% has distinctly reduced the formation of "Schiff's bases" on collagen incubated with glucose. This effect is significant at 0.03-0.1 and 0.3% and dose dependent. In conclusion, *Manilkara multinervis* extract according to example 1 at 0.03-0.3% has significantly reduced the formation of "Schiff's bases" on collagen incubated with glucose. Therefore *Manilkara multinervis* extract has presented an interesting potential to preserve collagen fibre quality and can be proposed as anti-aging ingredient.

Example 5

Anti-Elastase Effect of *Manilkara multinervis* Extract

The principle of this assay is the following: The assay is realized with an elastase from human leucocytes and a synthetic substrate (N-Methoxysuccinyl-(Ala)$_2$-Pro-Val-pNA). The products are solubilized with the enzyme and substrate in a buffer containing TRIS at 50 mM and TRITON X100 at 0.01%, (pH=7.5). After an incubation of 30 minutes, the quantity of hydrolysed substrate is measured by recording the optical density at 405 nm. The reference inhibitor is α1-antitrypsin. The results are expressed as a percentage of inhibition and IC50 (inhibitory concentration 50=concentration of product that inhibits at 50% the elastase activity) are calculated for each assay. Then the percentages and IC50 are presented as a mean+/−SEM (standard error of mean) on 3 assays and statistically evaluated by the student t test:

TABLE 3

Elastase inhibiting properties of *Manilkara multinervis* extract according to example 1

| Product | Dose | Mean | SEM | Student |
|---|---|---|---|---|
| Control | 0 | 0 | 0 | — |
| Alpha-1- | 0.002% | 79 | 5 | ** |
| Antitrypsin | 0.001% | 22 | 7 | * |
|  | 0.0005% | 7 | 3 | NS |
|  | 0.00025% | 3 | 1 | NS |
|  | 0.000125% | 3 | 0.2 | NS |
|  | IC50 (%) | 0.0015 | 0.0002 |  |
| *Manilkara* | 0.02% | 80 | 3 | ** |
| *multinervis* | 0.002% | 57 | 3 | ** |
| extract | 0.0002% | 9 | 4 | NS |
| according to | 0.00002% | 6 | 3 | NS |
| example 1 | 0.000002% | 6 | 3 | NS |
|  | IC50 (%) | 0.0018 | 0.0001 |  |

Statistics:
NS = not significant;
* = p < 0.05 (significant inhibition);
** = p < 0.01 (very significant inhibition)

These results demonstrate that *Manilkara multinervis* extract according to example 1 has shown a distinct potential to inhibit elastase, at the same level of activity as the endogenous inhibitor of elastase so called α1-antitrypsin (IC50=0.0015%). Therefore *Manilkara multinervis* extract can be proposed as anti-ageing ingredient in order to preserve the elasticity of mature skin.

Example 6

Pro-Collagen (Type I) Effect of *Manilkara multinervis* Extract

*Manilkara multinervis* extract according to example 1 was incubated on human dermal fibroblasts cultured in vitro and the release of collagen type I was measured in cell culture medium through an ELISA method. It was tested in comparison to the positive reference vitamin C (ascorbic acid).

The human dermal fibroblasts were cultured within growth medium enriched with Fetal Calf Serum (FCS) and incubated for 1 day at 37° C. Then the growth medium was exchanged for a standard medium containing FCS at 1% and the *Manilkara multinervis* extract according to example 1 and incubated for 3 days at 37° C. Thereafter, the cell number was measured by quantification of cellular proteins (Bradford's method) while the level of collagen synthesis was determined by quantification of collagen peptides in cell culture medium (ELISA method). The results were calculated through a reference range of proteins or collagen and then expressed in percentage referring to the control medium and presented as a mean+/−SEM (Standard Error of Mean) from 4 assays in triplicate.

TABLE 4

Pro-collagen (type I) effect of *Manilkara multinervis* extract according to example 1

|  | Cellular Proteins | Released type I Collagen |
|---|---|---|
| Control (=DMEM + FCS 1%) | 100 +/– 0 | 100 +/– 0 |
| Vitamin C at 5 µg/ml | 97 +/– 4 | 138 +/– 14** |
| *Manilkara multinervis* extract according to example 1 at 0.0003% | 82 +/– 8 | 142 +/– 6** |
| *Manilkara multinervis* extract according to example 1 at 0.001% | 92 +/– 11 | 120 +/– 18* |

Statistics (student t test):
* = significant effect ($p < 0.05$);
** = very significant effect ($p < 0.01$)

Vitamin C at 5 µg/ml has significantly increased the amount of released type I collagen/proteins without distinct modification of the level of cellular proteins. *Manilkara multinervis* extract according to example 1 at 0.0003% and 0.001% has significantly enhanced the amount of released type I collagen/proteins from cultured human dermal fibroblasts without distinct modification of the level of cellular proteins.

Example 7

Effect of *Manilkara multinervis* Extract on the Tropoelastin Synthesis

*Manilkara multinervis* extract according to example 1 was incubated on human dermal fibroblasts cultured in vitro and the synthesis of tropoelastin was measured in cell culture medium through an ICC method. It was tested in comparison to the positive reference TGF-β1 (Transforming Growth Factor-β1).

The human dermal fibroblasts were cultured within growth medium enriched with Fetal Calf Serum (FCS) and incubated for 3 days at 37° C. Then the growth medium was exchanged for a standard medium containing FCS at 1% and the *Manilkara multinervis* extract according to example 1 and incubated several days at 37° C. Thereafter, the tropoelastin synthesis was measured by immunocytochemistry (ICC) technique. The results were expressed in percentage of staining occupation and presented for 3 assays as a mean+/–SEM (Standard Error of Mean) of 6 measurements.

TGF-β1 at 10 ng/ml has significantly stimulated (mean of 82%) the tropoelastin synthesis by human dermal fibroblasts.

*Manilkara multinervis* extract according to example 1 at 0.002 and 0.006% has significantly stimulated in a dose-dependant way the tropoelastin synthesis by human dermal fibroblasts.

Example 8

Effect of *Manilkara multinervis* Extract on the EMILIN-1 Synthesis

EMILIN-1 (Elastin Microfibril Interface Located proteIN-1) also named Elastin microfibril interfacer 1 is an elastin associated protein. It is involved in different steps of the elastin fiber network formation.

*Manilkara multinervis* extract according to example 1 was incubated on human dermal fibroblasts cultured in vitro and the synthesis of EMILIN-1 was measured in cell culture medium through an ICC method.

The human dermal fibroblasts were cultured within growth medium enriched with Fetal Calf Serum (FCS) and incubated for 1 day at 37° C. Then the growth medium was exchanged for a standard medium containing FCS at 1% and the *Manilkara multinervis* extract according to example 1 and incubated for 2 days at 37° C. Thereafter, the EMILIN-1 synthesis was measured by immunocytochemistry (ICC) technique. The results were expressed in percentage of staining occupation and presented for 3 assays as a mean+/–SEM (Standard Error of Mean) of 6 measurements.

TABLE 6

Stimulation of EMILIN-1 expression by *Manilkara multinervis* extract

|  | % of staining occupation Assay 1 | % of staining occupation Assay 2 | % of staining occupation Assay 3 |
|---|---|---|---|
| Control (=DMEM + FCS 1%) | 0.43 +/– 0.06 | 1.3 +/– 0.21 | 1.32 +/– 0.21 |
| *Manilkara multinervis* extract according to example 1 at 0.002% | 2.1 +/– 0.38 (*) | 5.88 +/– 0.88 (*) | 4.27 +/– 0.41 (*) |

TABLE 5

Stimulation of tropoelastin synthesis by *Manilkara multinervis* extract

|  | % of staining occupation Assay 1 | % of staining occupation Assay 2 | % of staining occupation Assay 3 |
|---|---|---|---|
| Control (=DMEM + FCS 1%) | 7.05 +/– 1.82 | 4.22 +/– 1.13 | 1.99 +/– 0.74 |
| *Manilkara multinervis* extract according to example 1 at 0.002% | 20.54 +/– 3.89 (*) | 27.43 +/– 4.37 (*) | 34.57 +/– 5.29 (*) |
| *Manilkara multinervis* extract according to example 1 at 0.006% | 26.95 +/– 3.84 (*) | 36.22 +/– 4.28 (*) | 59.58 +/– 5.14 (*) |

Statistics (U Mann & Whitney):
(*) = significant effect/control ($p < 0.05$)

TABLE 6-continued

Stimulation of EMILIN-1 expression by *Manilkara multinervis* extract

|  | % of staining occupation Assay 1 | % of staining occupation Assay 2 | % of staining occupation Assay 3 |
|---|---|---|---|
| *Manilkara multinervis* extract according to example 1 at 0.006% | 5.28 +/− 1.17 (*) | 10.16 +/− 1.1 (*) | 5.43 +/− 0.35 (*) |

Statistics (U Mann & Whitney):
(*) = significant effect/control (p < 0.05)

*Manilkara multinervis* extract according to example 1 at 0.002 and 0.006% has significantly stimulated EMILIN-1 expression by human dermal fibroblasts and this effect is dose-dependent.

Example 9

Effect of *Manilkara multinervis* Extract on the Fibulin-5 Synthesis

Fibulin-5 is an extracellular matrix protein, an elastin associated protein that localizes to the surface of elastic fibres in vivo and regulates their assembly and organization.

*Manilkara multinervis* extract according to example 1 was incubated on human dermal fibroblasts cultured in vitro and the synthesis of fibulin-5 was measured in cell culture medium through an ICC method. It was tested in comparison to the positive reference TGF-$\beta$1 (Transforming Growth Factor-$\beta$1).

The human dermal fibroblasts were cultured within growth medium enriched with Fetal Calf Serum (FCS) and incubated for 3 days at 37° C. Then the growth medium was exchanged for a standard medium containing FCS at 1% and the *Manilkara multinervis* extract according to example 1 and incubated for 5 days at 37° C. Thereafter, the fibulin-5 synthesis was measured by immunocytochemistry (ICC) technique. The results were expressed in percentage of staining occupation and presented for 2 assays as a mean+/−SEM (Standard Error of Mean) of 6 measurements.

TABLE 7

Stimulation of fibulin-5 expression by *Manilkara multinervis* extract

|  | % of staining occupation Assay 1 | % of staining occupation Assay 2 |
|---|---|---|
| Control (=DMEM + FCS 1%) | 15.57 +/− 4.38 | 2.65 +/− 0.36 |
| TGF-$\beta$1 (mean only) | 79.99 | 18.8 |
| *Manilkara multinervis* extract according to example 1 at 0.002% | 35.8 +/− 4.0 (*) | 18.29 +/− 1.97 (*) |
| *Manilkara multinervis* extract according to example 1 at 0.006% | 43.8 +/− 4.84 (*) | 15.17 +/− 1.52 (*) |

Statistics (U Mann & Whitney):
(*) = significant effect/control (p < 0.05)

TGF-$\beta$1 at 10 ng/ml has significantly stimulated the fibulin-5 synthesis by human dermal fibroblasts.

*Manilkara multinervis* extract according to example 1 at 0.002 and 0.006% has significantly stimulated fibulin-5 expression by human dermal fibroblasts and this effect is dose-dependent.

The invention claimed is:

1. A cosmetic composition effective for improving skin firmness and ameliorating signs of aging, comprising:
   a) at least 0.0003% of an aqueous or alcoholic extract from fragmented leaves of *Manikara multinervis*, produced by the process consisting of:
      extracting the fragmented leaves of *Manikara multinervis* with water or an aqueous buffer at 60° C. or extracting said
      fragmented leaves of *Manikara multinervis* under reflux with 70% alcohol by volume in water to obtain a liquid extract;
      filtering the liquid extract; and optionally concentrating and/or drying the concentrated extract; and
   b) at least one cosmetically acceptable carrier.

2. The cosmetic composition of claim 1, wherein the cosmetically acceptable carrier is selected from the group consisting of at least one solvent, at least one surface-active substance and/or at least one wax component and/or at least one polymer and/or at least one oil component.

3. The cosmetic composition of claim 1 which comprises the extract of *Manilkara multinervis* leaves, in a concentration of from 0.0001 to 10%.

4. The cosmetic composition of claim 1, further comprising at least one additional skin and/or hair care active ingredient.

5. The cosmetic composition of claim 4, wherein the at least one additional skin and/or hair care active ingredient is selected from the group consisting of vitamins, peptides and peptide derivatives, sugar amines, UV-protective factors, flavonoid compounds, hair growth regulators, antioxidants and/or anti-oxidant precursors, preservatives, phytosterols, protease inhibitors, tyrosinase inhibitors, anti-inflammatory agents, and mixtures thereof.

6. The cosmetic composition of claim 1, wherein the concentrated aqueous extract is dried.

7. The cosmetic composition of claim 6, wherein the concentrated extract is spray-dried.

8. A method for preparing a *Manilkara multinervis* extract, the method consisting of water or aqueous buffer extraction of fragmented leaves of a *Manilkara multinervis* plant at 60° C. or 70% hydroalcoholic extraction under reflux, separation of a liquid extract from an insoluble fraction, filtration of the liquid extract, and optionally concentrating and/or drying the concentrated extract.

9. The method of claim 8, wherein the leaves are extracted with water with a pH from 4 to 8.

10. The method of claim 8, wherein the concentrated extract is dried.

11. The method of claim 10, wherein the concentrated extract is spray-dried.

12. A method of improving skin firmness and ameliorating signs of skin ageing comprising applying to skin in need thereof the cosmetic composition of claim 1.

13. The method of claim 12, wherein the signs of skin ageing include decrease of skin thickness, fine lines, wrinkles, loss of elasticity, sagging, and abnormal desquamation.

14. The method of claim 13, wherein application of the composition delays the development of wrinkles, diminishes the appearance of fine lines, improves the skin tone, ameliorates stretch marks, ameliorates the quality of scalp dermis, and/or fights against scalp ageing.

* * * * *